US007086286B1

(12) United States Patent
McCarey, Jr. et al.

(10) Patent No.: US 7,086,286 B1
(45) Date of Patent: Aug. 8, 2006

(54) TRANSDUCER HOLDER AND NOZZLE

(75) Inventors: Robert A. McCarey, Jr., Winthrop, MA (US); Christopher Frail, Ashland, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/160,120

(22) Filed: Jun. 9, 2005

(51) Int. Cl.
*G01D 11/30* (2006.01)
*G01N 29/02* (2006.01)
*G01N 29/30* (2006.01)

(52) U.S. Cl. ...................................... 73/632; 73/866.5
(58) Field of Classification Search ................. 73/632, 73/866.5
See application file for complete search history.

(56) References Cited

U.S. PATENT DOCUMENTS

| 5,189,332 | A | * | 2/1993 | Wild ........................... 310/345 |
| 5,440,937 | A | | 8/1995 | Lynnworth |
| 5,515,733 | A | | 5/1996 | Lynnworth |
| 5,814,736 | A | | 9/1998 | Loschberger |
| 6,343,511 | B1 | | 2/2002 | Lynnworth |
| 6,761,078 | B1 | | 7/2004 | Allen |
| 2003/0135084 | A1 | * | 7/2003 | Young ........................... 600/2 |
| 2005/0183739 | A1 | * | 8/2005 | McDermott et al. ........... 134/1 |

FOREIGN PATENT DOCUMENTS

EP        0 388 316 A2  *  9/1990

OTHER PUBLICATIONS

Manufacturers Standardization Society of the Valve Fittings Industry, Inc., "Integrally Reinforced Forged Branch Outlet Fittings—Socket Welding, Threaded, and Buttwelding Ends", MSS SP-97-2001:1-11.

* cited by examiner

*Primary Examiner*—Hezron Williams
*Assistant Examiner*—Rose M. Miller
(74) *Attorney, Agent, or Firm*—Cantor Colburn LLP

(57) ABSTRACT

A holder for a transducer having a sensor portion and a body portion is disclosed. The holder includes a base having an opening for receiving the transducer, a support member configured to support the transducer body portion with respect to the base, a noise suppression member disposed so as to suppress noise transmission between the base and the transducer sensor portion, and a compression member disposed to compress the noise suppression member to enhance noise suppression. The support member and the compression member are secured to the base independently from and mechanically in parallel to each other.

20 Claims, 6 Drawing Sheets

TRANSDUCER HOLDER AND NOZZLE

BACKGROUND OF THE INVENTION

The present disclosure relates generally to a transducer holder and nozzle, and particularly to a noise suppressing holder for use with an ultrasonic transducer.

Ultrasonic transducers are used in measurement systems that employ an electrically actuated signal source, typically a piezoelectric crystal, mounted in a mounting assembly fixed to a housing or wedge, or fixed directly to a conduit, to propagate ultrasonic signals through a medium flowing in the conduit. In applications where the medium has a low density, such as a gaseous medium, or where the size of the conduit or the signal path length through the medium raises considerations of crosstalk, the amount of signal energy that can be received through the medium is relatively small. Furthermore, because the signal propagates through the gas with a velocity different from and generally slower than its propagation velocity through the solid structure of the conduit, it can be difficult to find a suitable timing window in which the received signal can be dependably distinguished from ringing or other energy propagated directly through the conduit walls.

To some extent the problem of signal strength can be addressed by appropriate impedance matching and the use of a large-area diaphragm to couple the crystal to the medium. However, suitable isolation remains a problem, particularly in view of the relatively large amount of energy contained in the solid-path noise band. Accordingly, there is a need in the art for an ultrasonic transducer holder that addresses problems associated with crosstalk and short circuit noise.

BRIEF DESCRIPTION OF THE INVENTION

Embodiments of the invention include a holder for a transducer, where the transducer has a sensor portion and a body portion. The holder includes a base having an opening for receiving the transducer, a support member configured to support the transducer body portion with respect to the base, a noise suppression member disposed so as to suppress noise transmission between the base and the transducer sensor portion, and a compression member disposed to compress the noise suppression member to enhance noise suppression. The support member and the compression member are secured to the base independently from and mechanically in parallel to each other.

Other embodiments of the invention include a fluid flow measuring apparatus for use with a transducer, where the transducer has a sensor portion and a body portion. The apparatus includes a nozzle and an embodiment of the aforementioned holder. The nozzle is configured to connect with the holder and receive the transducer sensor portion.

Further embodiments of the invention include a holder for a transducer, where the transducer has a sensor portion and a body portion. The holder includes a base, a support member configured to support the transducer body portion with respect to the base, a noise suppression member disposed so as to suppress noise transmission between the base and the transducer sensor portion, and a compression member disposed to compress the noise suppression member in a non-rigid manner such that further compression of the noise suppression member is allowed. The base has a first through opening, the support member has a second through opening, the compression member has a third through opening, and the noise suppression member has a fourth through opening, the first, second, third and fourth through openings being axially aligned with an axis of the transducer for receiving the transducer therein. The support member and the compression member are secured to the base independently from and mechanically in parallel to each other, and the support member bridges the compression member.

BRIEF DESCRIPTION OF THE DRAWINGS

Referring to the exemplary drawings wherein like elements are numbered alike in the accompanying Figures.

DETAILED DESCRIPTION OF THE INVENTION

An embodiment of the invention provides a fluid flow measuring apparatus having a nozzle and a transducer holder for use with an ultrasonic transducer. The transducer holder includes a noise suppression member disposed to suppress short circuit noise across the transducer. A three-part transducer holder provides a means to secure the transducer, adjust the degree of compression of the noise suppression member, and securely couple the transducer to the nozzle. In an embodiment, the nozzle is a one-piece (unitary) nozzle for applications requiring accurate nozzle alignment. In an exemplary embodiment, the unitary nozzle is a one-piece forging, however, in another exemplary embodiment, the unitary nozzle may be fabricated using a manufacturing technique other than forging. While embodiments disclosed herein depict an ultrasonic transducer for use in measuring gaseous fluid flow, it will be appreciated that the disclosed invention is also applicable to other transducer applications, such as a liquid fluid flow measuring apparatus for example.

Figure 1:
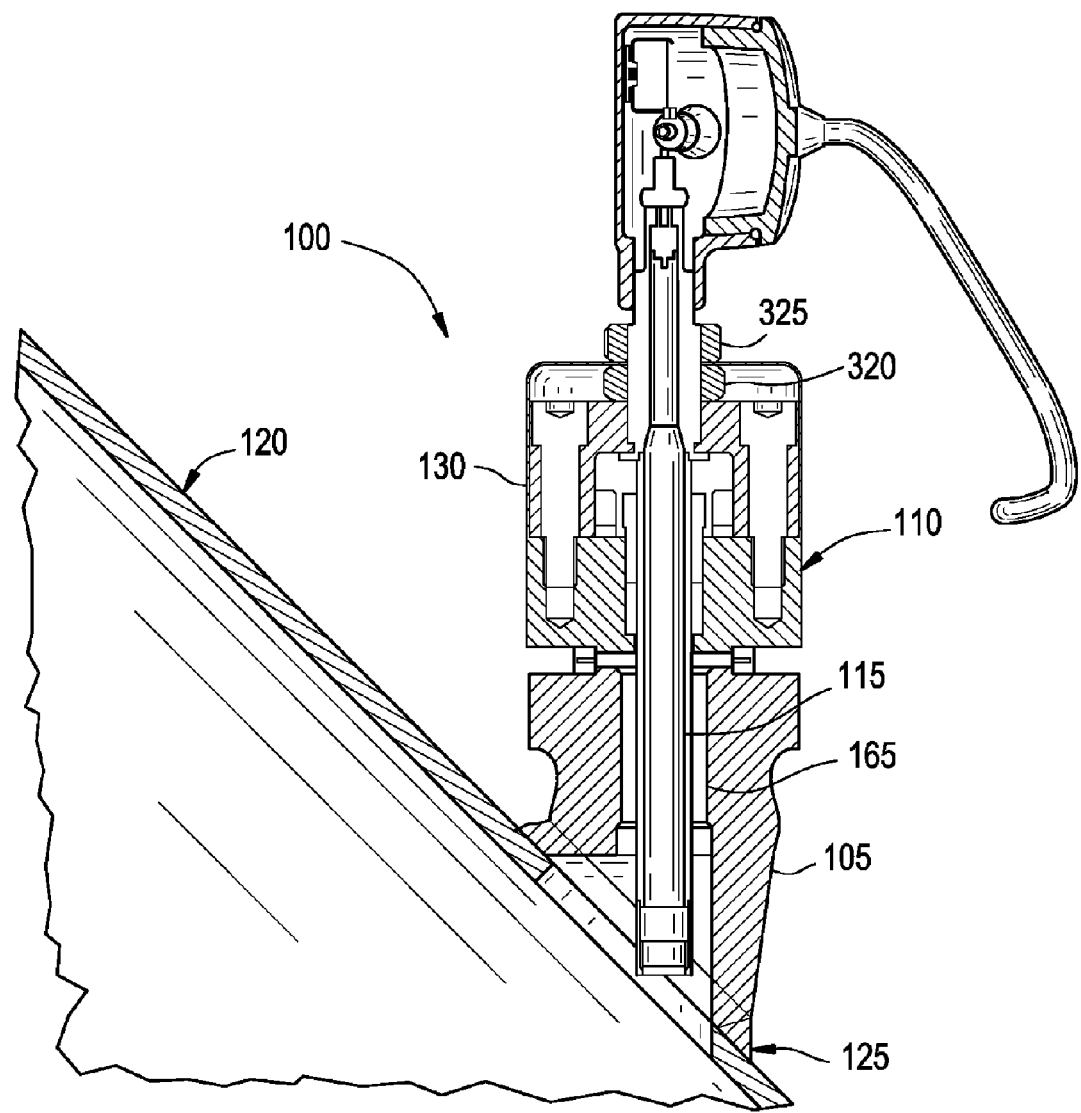
FIG. 1 depicts an exemplary fluid flow measuring apparatus in accordance with an embodiment of the invention, with some parts illustrated in a translucent fashion to show internal parts.

FIG. 1 is an exemplary embodiment of a fluid flow measuring apparatus 100 having a nozzle 105 and a transducer holder 110 for holding a transducer 115, such as an ultrasonic transducer for example, and is illustrated in a translucent fashion to show internal parts. More particularly, housing 130 of holder 110 and nozzle 105 are illustration in a translucent fashion. In an embodiment, housing 130 is secured to transducer 115 via hardware 325. In a typical application, nozzle 105 is welded to a cylindrical header pipe 120 at interface surface 125.

Figure 2:
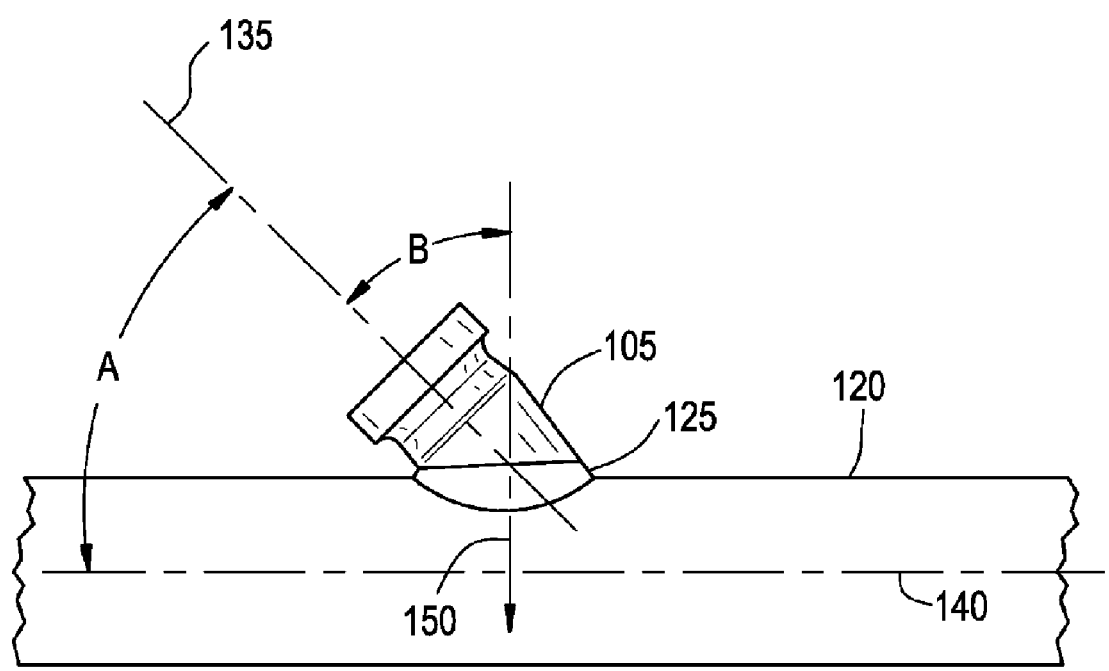
FIG. 2 depicts a side view of an exemplary nozzle connected to an exemplary header pipe for use in accordance with an embodiment of the invention.

FIG. 2 illustrates a side view of header pipe 120 with nozzle 105 welded at interface surface 125 such that the axial centerline 135 of nozzle 105 is at an angle "A" with respect to the axial centerline 140 of header pipe 120. As a result, the opening 145 (best seen by referring to FIG. 3) has a direction vector 150 that is at an angle "B" relative to the axial centerline 135 of nozzle 105.

Figure 3:
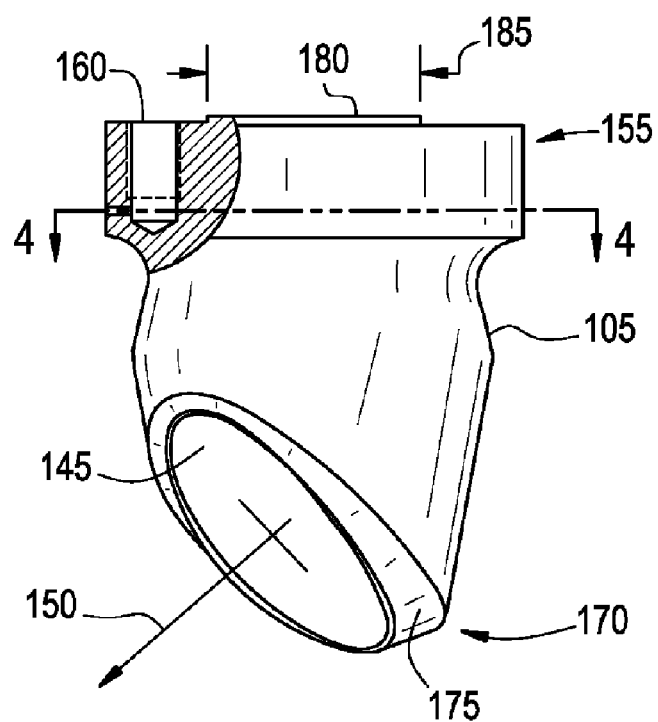
FIG. 3 depicts a side view of an exemplary nozzle in accordance with an embodiment of the invention.
Figure 4:
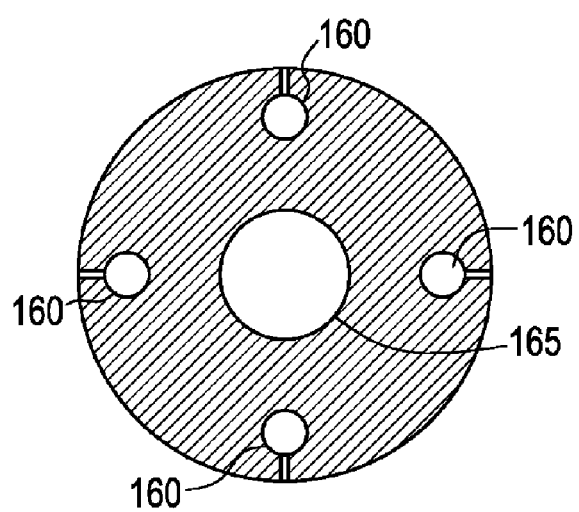
FIG. 4 depicts a section cut through the nozzle of FIG. 3.

Referring now to FIGS. 1, 3 and 4 collectively, an embodiment of nozzle 105 is a unitary structure made from one piece having a first end 155, a second end 170, and an axial through hole 165 extending from the first end 155 to the second end 170. Opening 145 at the second end 170 provides for unobstructed signal communication between transducer 115 and the flow field within header pipe 120, the transducer 115 being disposed within axial through hole 165. At the first end 155 of nozzle 105 is a set of blind holes 160 for receiving hardware 270 (best seen by referring to FIG. 5) that secures holder 110 to nozzle 105. Around the perimeter of the opening 145 at the second end 170 there is an outlet surface 175 that is configured to mate with and be welded to an exterior surface of the cylindrical header pipe 120. The angle of opening 145 defines the direction vector 150 that is angled with respect to axial through hole 165. At the first end 155 there is a raised surface 180 that is concentric with the axial through hole 165 and has an outside diameter 185 that is inboard of the set of blind holes 160. Raised surface 180 provides a mating surface for mounting holder 110, which will now be discussed in more detail with reference to FIGS. 5–9.

Figure 5:
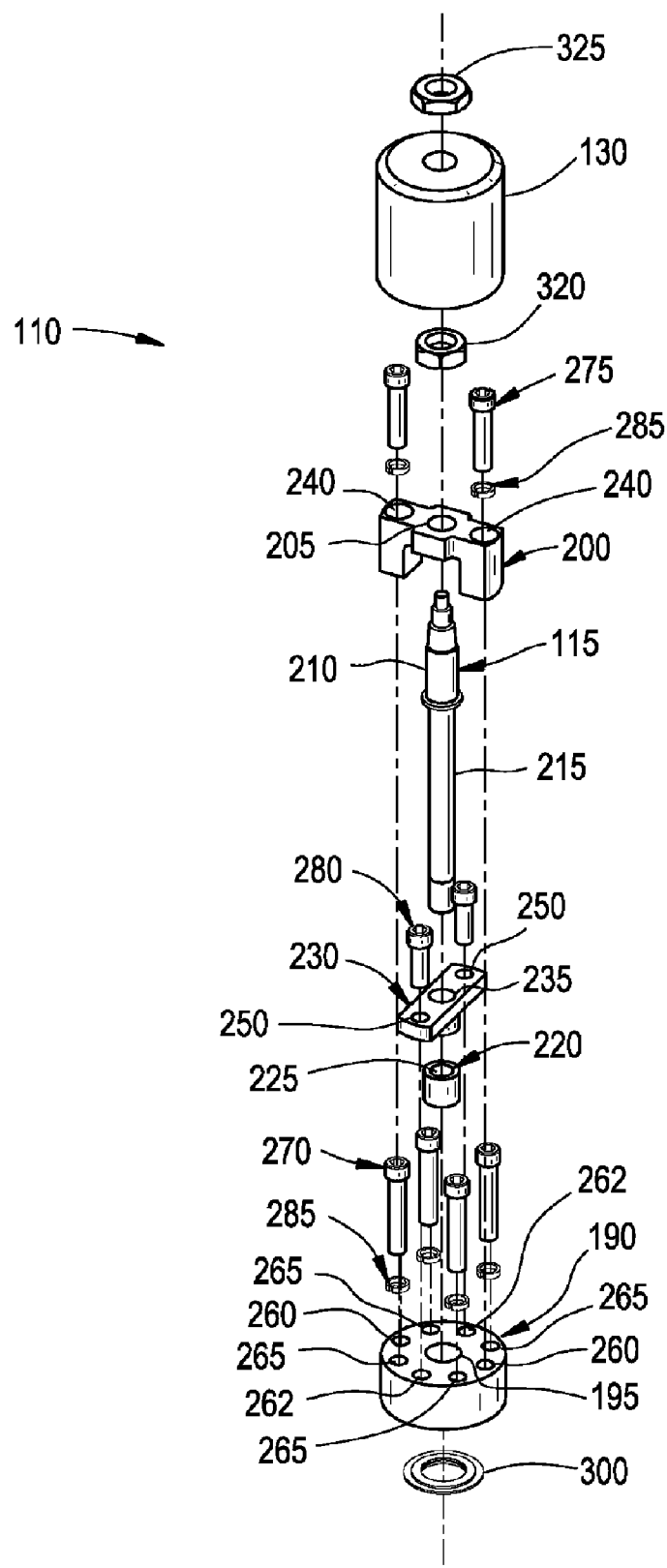
FIG. 5 depicts an exploded assembly view of a transducer holder in accordance with an embodiment of the invention.

Referring to FIG. 5, an exploded assembly view of holder 110 is depicted with transducer 115, which has a body portion 210 and a sensor portion 215. Holder 110 includes four primary members: a base 190 having a through opening 195 for receiving the sensor portion 215 of transducer 115; a support member 200 having a through opening 205 and being configured to support the body portion 210 of transducer 115 with respect to the base 190 via hardware 320; a noise suppression member 220 having a through opening 225 and being disposed so as to suppress noise transmission between the base 190 and the transducer sensor portion 215; and a compression member 230 having a through opening 235 and being disposed to compress the noise suppression member 220 between the base 190 and the outer surface of sensor portion 215 to enhance noise suppression to sensor portion 215.

Figure 6:
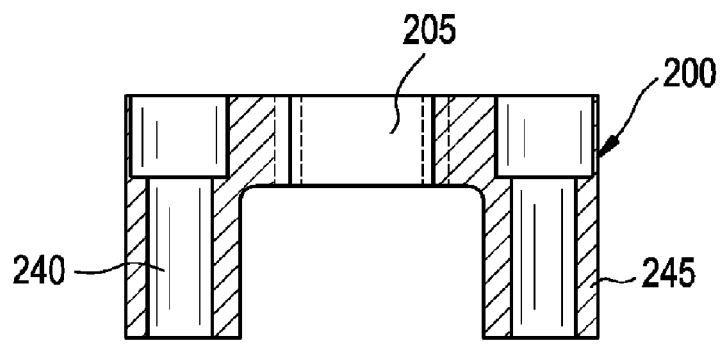
FIGS. 6–8 depict section views of parts of the transducer holder of FIG. 5.
Figure 7:
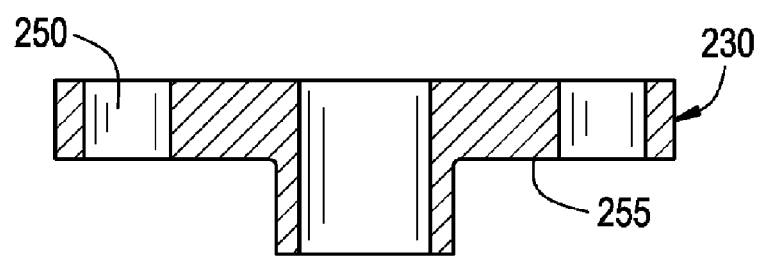
Figure 8:
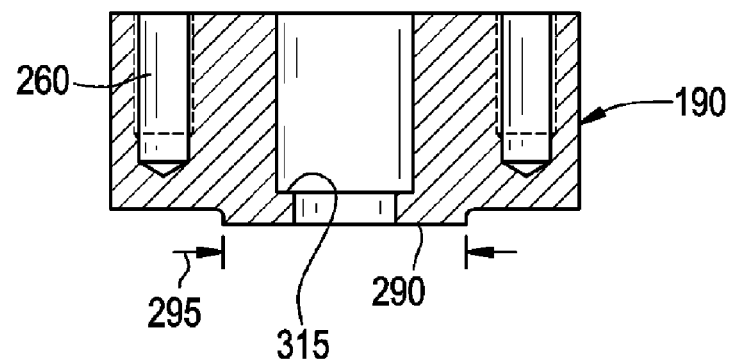

In FIG. 6, support member 200 is depicted in cross section view with the section cut being taken through mounting holes 240 of side legs 245. In FIG. 7, compression member 230 is depicted in cross section view with the section cut being taken through mounting holes 250 of side arms 255. In FIG. 8, base 190 is depicted in cross section view with the section cut being taken through blind mounting holes 260. Base 190 also includes four through holes 265 for receiving mounting hardware 270 that secures base 190 to nozzle 105 via blind holes 160 in nozzle 105 (see FIG. 3). Mounting hardware 275 secures support member 200 to base 190 via through holes 240 and blind holes 260, and mounting hardware 280 secures compression member 230 to base 190 via through holes 250 and blind holes 262. Lock washers 285 are used with mounting hardware 275, 285 as appropriate.

As illustrated in FIG. 5, support member 200 is arranged on base 190 through one pair of mounting holes 260, and compression member 230 is arranged on base 190 through a second pair of mounting holes 262 that are oriented ninety degrees with respect to the first pair of mounting holes. As such, support member 200 and compression member 230 are secured to base 190 independently from and mechanically in parallel to each other. In an embodiment, the support member 200 is disposed to bridge the compression member 230.

Referring back to FIG. 8, base 190 includes a raised mating surface 290 having a diameter 295 that mates with and mirrors the diameter 185 of the raised mating surface 180 of nozzle 105. In an embodiment, a gasket 300 may be disposed between raised surface 180 and raised surface 290. Through holes 265 of base 190 are aligned with blind holes 160 of nozzle 105 such that mounting hardware 270 fixedly secures base 190, and therefore holder 110, to the first end 155 of nozzle 105.

Figure 9:
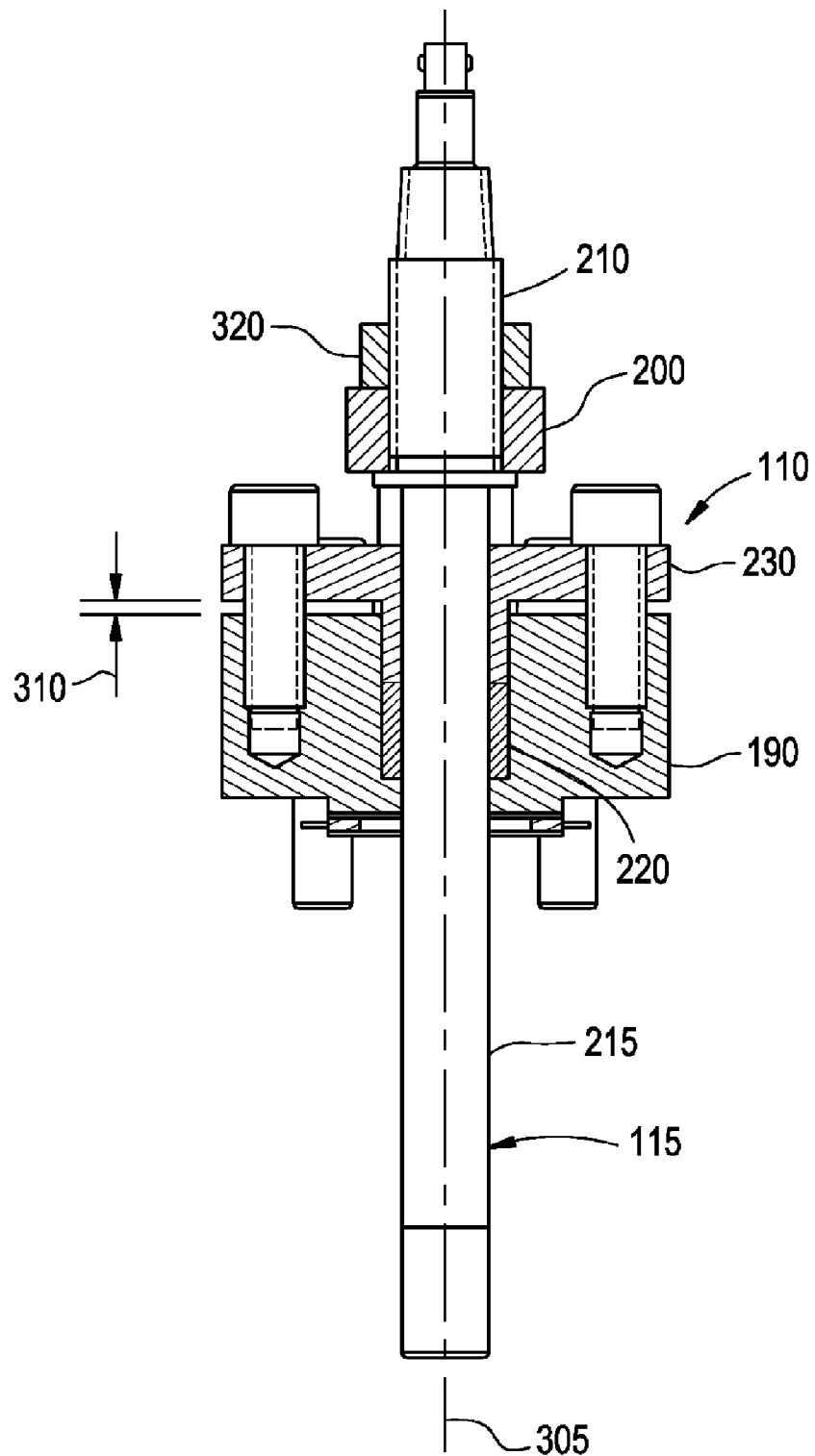
FIG. 9 depicts a section view of the transducer holder of FIG. 5 in an assembled state.

Reference is now made to FIGS. 5 and 9, where FIG. 9 depicts a cross section view of holder 110 in an assembled state with the section being through the mounting holes 250 of compression member 230. As depicted, the through opening 195 of base 190, the through opening 205 of support member 200, the through opening 235 of compression member 230, and the through opening 225 of noise suppression member 220, are all axially aligned with the axis 305 of the transducer 115, thereby enabling transducer 115 to be received therein. In the assembled state, noise suppression member 220 is disposed so as to be between the base 190 and the transducer sensor portion 215, and the compression member 230 is disposed so as to compress the noise suppression member 220 in a non-rigid manner such that further compression of the noise suppression member 220 is allowed, as illustrated by the clearance gap 310 between compression member 230 and base 190. In an embodiment, noise suppression member 220 is sized such that a clearance gap 310 of about 0.12 inches results, thereby enabling adjustment of the degree of compression during routine maintenance.

By employing a cylindrically shaped noise suppression member 220 that sits in a pocket 315 of base 190 (best seen by referring to FIG. 8), and is disposed around sensor portion 215, noise suppression member 220 not only suppresses short circuit noise that may be transmitted from base 190 to sensor portion 215, but also serves to suppress fluid flow between the base 190 and the sensor portion 215 originating from the flow field within header pipe 120.

In an embodiment, the noise suppression member 220 is made from a compressible material suitable for operating at a temperature equal to or greater than about –328 degrees Fahrenheit and equal to or less than about 850 degrees Fahrenheit, and suitable for sealing fluid pressures equal to or greater than about 0 psi and equal to or less than about 10,000 psi. An exemplary suitable material is 9000-S EVSP Garlock packing material available from Garlock Sealing Technologies.

As disclosed, some embodiments of the invention may include some of the following advantages: a transducer holder having an integrally arranged noise suppression member; a transducer holder having a support member that secures the transducer independent from a compression member that compresses a noise suppression member, thereby enabling separate adjustments for the securing function and the noise suppression function; a transducer holder allowing for compression adjustment of the noise suppression member subsequent to assembly; and, a unitary nozzle made from one piece that serves to reduce the effect of multi-part fit-up tolerances in critical alignment applications.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A holder for a transducer, the transducer having a sensor portion and a body portion, the holder comprising:
   a base having an opening for receiving the transducer;
   a support member configured to support the transducer body portion with respect to the base;
   a noise suppression member disposed so as to suppress noise transmission between the base and the transducer sensor portion; and
   a compression member disposed to compress the noise suppression member to enhance noise suppression;
   wherein the support member and the compression member are secured to the base independently from and mechanically in parallel to each other.

2. The holder of claim 1, wherein:
   the compression member is disposed to compress the noise suppression member between the base and the transducer sensor portion.

3. The holder of claim 1, wherein:
   the compression member is disposed to compress the noise suppression member in a non-rigid manner such that further compression of the noise suppression member is allowed.

4. The holder of claim 1, wherein:
   the support member and the compression member are secured to the base via blind holes at the base.

5. The holder of claim 1, wherein:
   the noise suppression member is disposed so as to be between the base and the transducer sensor portion.

6. The holder of claim 1, wherein:
   the base opening comprises a first through opening;
   the support member comprises a second through opening;
   the compression member comprises a third through opening;
   the noise suppression member comprises a fourth through opening; and
   the first, second, third and fourth through openings are axially aligned with an axis of the transducer for receiving the transducer therein.

7. The holder of claim 1, wherein:
   the noise suppression member is disposed so as to suppress fluid flow between the base and the transducer sensor portion.

8. The holder of claim 1, wherein:
   the support member bridges the compression member.

9. The holder of claim 1, wherein:
   the noise suppression member comprises a compressible material suitable for operating at a temperature equal to or greater than about −328 degrees Fahrenheit and equal to or less than about 850 degrees Fahrenheit.

10. The holder of claim 7, wherein:
    the noise suppression member comprises a compressible material suitable for operating at a temperature equal to or greater than about −328 degrees Fahrenheit and equal to or less than about 850 degrees Fahrenheit, and suitable for sealing fluid pressures equal to or greater than about 0 psi and equal to or less than about 10,000 psi.

11. The holder of claim 3, wherein:
    the further allowed compression is about 0.12 inches.

12. A fluid flow measuring apparatus for use with a transducer, the transducer having a sensor portion and a body portion, the apparatus comprising:
    a nozzle; and
    a holder for holding the transducer, the holder comprising:
    a base having an opening for receiving the transducer;
    a support member configured to support the transducer body portion with respect to the base;
    a noise suppression member disposed so as to suppress noise transmission between the base and the transducer sensor portion; and
    a compression member disposed to compress the noise suppression member to enhance noise suppression;
    wherein the support member and the compression member are secured to the base independently from and mechanically in parallel to each other; and
    wherein the nozzle is configured to connect with the holder and receive the transducer sensor portion.

13. The apparatus of claim 12, wherein:
    the nozzle is a unitary structure.

14. The apparatus of claim 12, wherein:
    the nozzle comprises a first end having a set of blind holes and the base comprises a set of through holes, the through holes and blind holes being aligned and configured to receive hardware to secure the base to the first end of the nozzle.

15. The apparatus of claim 14, wherein:
    the nozzle further comprises a second end and an axial through hole extending from the first end to the second end, the axial hole being configured to receive the transducer sensor portion.

16. The apparatus of claim 15, wherein:
    the perimeter of the second end of the nozzle comprises an outlet surface configured to mate with an exterior surface of a cylindrical header pipe.

17. The apparatus of claim 16, wherein:
    the outlet surface defines an orifice having a direction vector that is angled relative to the axial through hole.

18. The apparatus of claim 15, wherein:
    the first end of the nozzle comprises a raised mating surface concentric with the axial through hole and having an outside diameter that is inboard of the set of blind holes.

19. The apparatus of claim 18, wherein:
    the base comprises a raised mating surface that mates with and mirrors the diameter of the raised mating surface of the nozzle.

20. A holder for a transducer, the transducer having a sensor portion and a body portion, the holder comprising:
    a base;
    a support member configured to support the transducer body portion with respect to the base;
    a noise suppression member disposed so as to suppress noise transmission between the base and the transducer sensor portion; and
    a compression member disposed to compress the noise suppression member in a non-rigid manner such that further compression of the noise suppression member is allowed;
    wherein the base has a first through opening, the support member has a second through opening, the compression member has a third through opening, and the noise suppression member has a fourth through opening, the first, second, third and fourth through openings being axially aligned with an axis of the transducer for receiving the transducer therein;

wherein the support member and the compression member are secured to the base independently from and mechanically in parallel to each other; and wherein the support member bridges the compression member.

* * * * *